US010500318B1

(12) United States Patent
Robertson

(10) Patent No.: US 10,500,318 B1
(45) Date of Patent: Dec. 10, 2019

(54) DOSING REGIMENS FOR TREATING HYPOXIA-ASSOCIATED TISSUE DAMAGE

(71) Applicant: Temple Therapeutics BV, Geleen (NL)

(72) Inventor: Lynne M. Robertson, North Smithfield, RI (US)

(73) Assignee: Temple Therapeutics BV, Geleen (NL)

( * ) Notice: Subject to any disclaimer, the term of this patent is extended or adjusted under 35 U.S.C. 154(b) by 0 days.

(21) Appl. No.: 16/027,080

(22) Filed: Jul. 3, 2018

(51) Int. Cl.
| | |
|---|---|
| *A61K 31/198* | (2006.01) |
| *A61K 38/05* | (2006.01) |
| *A61L 31/16* | (2006.01) |
| *A61L 31/14* | (2006.01) |
| *A61L 31/04* | (2006.01) |
| *A61K 9/00* | (2006.01) |

(52) U.S. Cl.
CPC ............ *A61L 31/16* (2013.01); *A61K 9/0014* (2013.01); *A61K 31/198* (2013.01); *A61K 38/05* (2013.01); *A61L 31/047* (2013.01); *A61L 31/145* (2013.01); *A61L 31/148* (2013.01); *A61L 2300/214* (2013.01); *A61L 2300/25* (2013.01); *A61L 2300/412* (2013.01); *A61L 2300/424* (2013.01)

(58) Field of Classification Search
CPC ..... A61K 9/0014; A61K 31/198; A61K 38/05
See application file for complete search history.

(56) References Cited

U.S. PATENT DOCUMENTS

| | | | |
|---|---|---|---|
| 5,693,671 A | 12/1997 | Niihara et al. | |
| 6,613,070 B2 | 9/2003 | Redmond et al. | |
| 6,638,949 B1 | 10/2003 | Folkman et al. | |
| 6,797,729 B1 | 9/2004 | Byrne et al. | |
| 6,852,541 B2 | 2/2005 | Obayan et al. | |
| 8,759,298 B2 | 6/2014 | Rosa et al. | |
| 8,785,395 B2 | 7/2014 | Prockop et al. | |
| 9,011,883 B2 * | 4/2015 | Obayan ............... | A61K 9/0019 424/400 |
| 9,062,103 B2 | 6/2015 | Prockop et al. | |
| 9,090,704 B2 | 7/2015 | Rosa et al. | |
| 9,498,517 B2 | 11/2016 | Rosa et al. | |
| 9,545,428 B2 | 1/2017 | Prockop et al. | |
| 9,730,961 B2 | 8/2017 | Prockop et al. | |
| 9,849,154 B2 * | 12/2017 | Castex-Rizzi ....... | A61K 9/0014 |
| 10,105,396 B2 | 10/2018 | Prockop et al. | |
| 2015/0265675 A1 | 9/2015 | Prockop et al. | |
| 2017/0014358 A1 * | 1/2017 | Tuffley ............... | A61K 31/155 |
| 2017/0145385 A1 | 5/2017 | Prockop et al. | |
| 2018/0236035 A1 | 8/2018 | Rosa | |
| 2018/0296631 A1 * | 10/2018 | Radisic ............. | A61K 47/6953 |

FOREIGN PATENT DOCUMENTS

WO 2014053542 A1 4/2014

OTHER PUBLICATIONS

Bohme, "Drug Delivery and Release Systems for Targeted Tumor Therapy," J. Pept. Sci., 2015, vol. 21, pp. 186-200.
De Oliveira et al., "Intravenous glutamine administration reduces lung and distal organ injury in malnourished rats with sepsis," Shock 41(3):222-32 (2014) doi: 10.1097/SHK.0000000000000102.
Hoare, "Hydrogels in Drug Delivery: Progress and Challenges," Polymer, 2008, vol. 29, pp. 1993-2007.
Lehmann et al., "Intravenous free and dipeptide-bound glutamine maintains intestinal microcirculation in experimental endotoxemia," Nutrition 28(5):588-593 (2012) doi: 10.1016/j.nut.2011.09.021.
Robertson et al., "Evitar (L-Alanyl-L-Glutamine) Regulates Key Signaling Molecules in the Pathogenesis of Postoperative Tissue Fibrosis," Reprod Sci. Sep 5:1933719118789511 (2018) doi: 10.1177/1933719118789511.
Strowitzki et al., "Pharmacological HIF-inhibition attenuates postoperative adhesion formation," Nature Sci. Rep. 7(1): 13151 (2017); doi: 10.1038/s41598-017-13638-z.

\* cited by examiner

*Primary Examiner* — Jeffrey E. Russel
(74) *Attorney, Agent, or Firm* — Brinks Gilson & Lione

(57) ABSTRACT

Described herein are methods for the treatment of hypoxia-associated tissue damage in subjects. More particularly, the methods relate to treating hypoxia-associated tissue damage in a subject during a surgical procedure with a therapeutically effective amount of a glutamine source comprising glutamine, a dipeptide comprising glutamine, or a glutamine amino ester conjugate according to particular dosing regimens. Specifically, the methods concern a dosing scheme comprising dosing a subject during a surgical procedure with a glutamine source wherein the first dose is administered to the subject within about 30 minutes following an initial surgical incision made during the surgical procedure, one or more additional doses of the glutamine source is administered at fixed intervals of time after the first dose, and one or more doses is administered just prior to closure of all surgical incisions.

25 Claims, No Drawings

DOSING REGIMENS FOR TREATING HYPOXIA-ASSOCIATED TISSUE DAMAGE

TECHNICAL FIELD

The present invention relates to the treatment of hypoxia-associated tissue damage in subjects. More particularly, the methods relate to treating hypoxia-associated tissue damage in a subject during a surgical procedure according to particular dosing regimens. Specifically, the methods concern a dosing scheme comprising dosing a subject during a surgical procedure wherein a first dose is administered to the patient within about 120 minutes following an initial surgical incision made during the surgical procedure and optionally dosing the subject one or more times following the initial incision and/or dosing the subject again just prior to closure of all surgical incisions.

BACKGROUND

Post-surgical adhesions are a significant cause of postoperative pain and other surgical complications. Oxidative stress and hypoxia play an important role in adhesion formation. Hypoxia triggers a cascade of responses that ultimately lead to adhesion formation. Development of adhesions is a multistep process, comprising a macrophage-driven inflammatory response, formation of a fibrinous exudate, recruitment of fibroblasts that become activated to form myofibroblasts, excess collagen fiber deposition and subsequent vascularization. These processes occur in a low oxygen environment (hypoxia), which critically modulates inflammation and healing. On the molecular level, responses to hypoxia are orchestrated by hypoxia-inducible factors (HIFs), consisting of an oxygen-dependent α- (HIF-1α, HIF-2α) and an oxygen-independent β-subunit. HIF-α-subunits are constitutively expressed and rapidly degraded in normoxia. In hypoxia, however, HIF-1α and HIF-2α are stabilized and form active transcription complexes. The complexes bind to hypoxia response elements (HRE) in the promoter region of numerous downstream target genes, which collectively mount the adaptive response to hypoxia.

Under normoxic conditions, glucose is catabolized intracellularly to form pyruvate, which is further metabolized to produce adenosine triphosphate (ATP) via the citric acid cycle (TCA cycle). Conversely, under hypoxic conditions, the amount of pyruvate entering the TCA cycle is decreased and pyruvate is converted to lactate. Anaerobic glycolysis is activated by hypoxia-inducible factors (HIFs), which shift metabolism towards anaerobic glycolysis by altering glycolytic enzymes. HIFs inhibit pyruvate dehydrogenase, which converts pyruvate into acetyl CoA, and stimulate lactate dehydrogenase (LDH), which converts pyruvate into lactate; thus leading to increased production of lactate. Lactate may be crucial to adhesion formation through stimulation of other factors involved in adhesion formation such as VEGF and collagen.

U.S. Pat. No. 9,011,883 describes methods for treating or reducing adhesions in the peritoneum of a patient comprising administering an effective amount of L-glutamine or a dipeptide comprising alanyl-glutamine during or after a surgical procedure that affects the peritoneum of the patient.

Recently, it was reported that a single intraoperative lavage with a HIF-1α inhibitor (20 mg/kg) reduced adhesion formation in a mouse model [Strowitzki, M. J., et al., Sci Rep, 2017. 7(1): p. 13151]. The results in vivo were confirmed at the cellular level, where hypoxic up-regulation of several biomarkers of inflammation, including HIF-1α and TGF-β, was blunted in normal murine peritoneal fibroblasts in vitro upon treatment with micromolar doses of a HIF-1α inhibitor.

There is a need in the art for compounds and methods for treating and preventing adhesions, and more particularly hypoxia-associated tissue damage.

BRIEF SUMMARY OF THE INVENTION

Described herein are methods for treating hypoxia-associated tissue damage in subjects. In certain embodiments, the tissue damage is a result of a surgical procedure.

In one embodiment, the invention provides methods for treating or preventing tissue adhesions in a subject that is undergoing a surgical procedure, the method comprising administering to the subject during the surgical procedure a therapeutically effective amount of a glutamine source topically to a tissue that is subject to adhesion formation, wherein the first dose of the glutamine source is administered within about 120 minutes after an initial surgical incision during the surgical procedure.

In another embodiment, the invention provides methods for treating or preventing hypoxia-associated tissue damage in a subject that is undergoing a surgical procedure, the method comprising administering to the subject during the surgical procedure a therapeutically effective amount of a glutamine source topically to a tissue subject to hypoxia-associated tissue damage, wherein the first dose of the glutamine source is administered within about 120 minutes after an initial surgical incision during the surgical procedure.

In another embodiment, the invention provides methods for reducing HIF-1α in hypoxia-associated damaged tissue in a subject that is undergoing a surgical procedure, the method comprising administering to the subject during the surgical procedure a therapeutically effective amount of a glutamine source topically to the damaged tissue, wherein the first dose of the glutamine source is administered within about 120 minutes after an initial surgical incision during the surgical procedure.

DETAILED DESCRIPTION OF THE INVENTION

The following paragraphs define in more detail the embodiments of the invention described herein. The following embodiments are not meant to limit the invention or narrow the scope thereof, as it will be readily apparent to one of ordinary skill in the art that suitable modifications and adaptations may be made without departing from the scope of the invention, embodiments, or specific aspects described herein. All patents and publications cited herein are incorporated by reference herein in their entirety.

The term "glutamine source" or "source of glutamine" includes glutamine and its physiologically acceptable salts, as well as glutamine conjugates and peptides comprising glutamine as described further herein.

The terms "dosage" or "dose" or "dosage form" as used herein denote any form or formulation of the glutamine source that contains an amount sufficient to produce a therapeutic effect with a single administration or multiple administrations.

The term "surgical incision" as used herein means a wound made by a cutting instrument such as a scalpel, laser, or other cutting instrument prior to or during a surgical procedure, including incisions or points of entry made for laparoscopic or other minimally invasive surgical techniques.

The term "prevention of" as used herein includes the meaning of reducing. The amount of the reduction may be from about 0.001% to about 100%.

The term "effective amount" is an amount that achieves the desired effect. For example, in the present invention, the effective amount of one or more glutamine sources is an amount that, after one or more administrations, reduces or prevents hypoxia-associated tissue damage. In some embodiments, the effective amount is an effective amount of a source of glutamine that prevents or reduces adhesion in one or more tissues.

The term "drug load" as used herein refers to the wt % of the glutamine source relative to the total mass of the dosage form.

The terms "formulation" or "composition" as used herein refers to the glutamine source in combination with one or more pharmaceutically acceptable diluents and/or excipients.

The terms "extended release" or "sustained release" as used herein refers to a composition that releases an active ingredient according to a desired profile over an extended period under physiological conditions or in an in vitro test. By "extended period" it is meant a continuous period of time of at least about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically over a period of about 18 hours under physiological conditions or in an in vitro assay.

The term "delayed" release" as used herein refers to a composition that releases an active ingredient after a period of time, for example minutes or hours, such that the active ingredient is not released initially. A delayed release composition may provide, for example, the release of a drug or active ingredient from a dosage form, after a certain period, under physiological conditions or in an in vitro test.

The term "treating" refers to administering a therapy in an amount, manner, or mode effective (e.g., a therapeutic effect) to improve a condition, symptom, disorder, or parameter associated with a disorder, or a likelihood thereof. In some embodiments, the term treating refers to the treatment or prevention of adhesion formation following surgery. In other embodiments, the term treating refers to the treatment or prevention of hypoxia-associated tissue damage in a patient undergoing a surgical procedure.

The term "prophylactically treating" refers to administering a therapy in an amount prior to incurring a condition, symptom, disorder, or parameter associated with a disorder, or reducing the likelihood thereof.

The term "subject" refers to any mammal, including animals and humans. The subject may be a medical patient in need of treatment thereof. In one embodiment, the subject is a human.

The term "preventing" or "reducing" refers to preventing or reducing the progression of a disorder, such as adhesion, either to a statistically significant degree or to a degree detectable to one skilled in the art.

The term "substantially" as used herein means to a great or significant extent, but not completely.

As used herein, "a" or "an" means one or more unless otherwise specified.

Terms such as "include," "including," "contain," "containing," "having," and the like mean "comprising."

Described herein are methods for treating hypoxia-associated tissue damage and, in particular, preventing or treating adhesion formation in a patient that is undergoing a surgical procedure by administering a glutamine source at a particular time following the initial surgical incision made during the surgical procedure, or at multiple times during the surgical procedure if the procedure exceeds a certain length of time. Injury to tissues, including surgical operations, leads to an inflammatory response, which results in fibrin deposition and subsequent fibrinous adhesion. If this adhesion is not prevented or degraded shortly after injury stemming from surgery or other injury, reparative cells including fibroblasts propagate into the fibrin matrix turning it into permanent fibrous adhesion. While not being bound by any particular theory, the inventors have surprisingly found that administering a glutamine source within about 60 to about 120 minutes following the initiation of hypoxia reduces the amount of HIF-1α protein in the cells subjected to hypoxia. Although earlier or later administration of a glutamine source does have some effect on levels of HIF-1α protein, a greater effect is seen when the glutamine source is administered within about 60 to about 120 minutes after the initiation of hypoxia.

Accordingly, described herein are methods for treating or preventing adhesions, hypoxia-associated tissue damage, or reducing HIF-1α in hypoxia-associated damaged tissue in a subject that is undergoing a surgical procedure, the methods comprising administering to the subject during the surgical procedure a therapeutically effective amount of a glutamine source topically to a tissue subject to hypoxia-associated tissue damage, wherein the first dose of the glutamine source is administered within about 120 minutes after an initial surgical incision during the surgical procedure. In certain embodiments, the first dose of the glutamine source is administered within about 90 minutes after an initial surgical incision during a surgical procedure. In another embodiment, the first dose of the glutamine source is administered within about 30 minutes to about 120 minutes, within about 60 minutes to about 120 minutes, within about 30 minutes to about 90 minutes, or within about 30 minutes to about 60 minutes. In a further embodiment, the glutamine source is administered within about 60 minutes.

The methods described herein comprise administering a glutamine source to a subject at least once within a specified period of time. In certain embodiments, the glutamine source is administered to the subject more than once. For example, the subject may receive a first dose of the glutamine source within a specified period of time followed by one or more additional doses of the glutamine source at specified periods of time, at fixed intervals of time, and/or just prior to closure of all surgical incisions. The number of additional doses of the glutamine source can be at the discretion of the surgeon, but generally the number of doses of the glutamine source is dependent upon the overall length of the surgery or the amount of time the affected tissue is subject to hypoxia-associated damage. In one embodiment, an additional dose of the glutamine source is administered to the subject just prior to closure of all surgical incisions. In certain embodiments, the additional dose or doses of the glutamine source is administered at fixed intervals of time. The intervals of time can be any interval of time but is preferable an interval of time from about 15 minutes to about 120 minutes, from about 30 minutes to about 120 minutes, from about 30 minutes to about 90 minutes, from about 30 minutes to 60 minutes, or more particularly, about every 90 minutes, about every 60 minutes, about every 45 minutes, or about every 30 minutes, following the time of the initial dose the glutamine source.

Glutamine is a conditionally essential amino acid that is well absorbed, enhances wound healing, and modulates the function of neutrophils, macrophages, and lymphocytes. It also serves as a substrate for production of the antioxidant glutathione. During periods of catabolic stress (trauma, sepsis, burn), glutamine is released from muscle stores into the serum and intracellular levels of glutamine in muscle decrease. The tissues, particularly in splanchnic organs, rapidly take up the glutamine and glutamine serum concentrations subsequently fall. Previous work has demonstrated the efficacy of glutamine containing solutions in preventing peritoneal adhesion formation in a rat model (U.S. Pat. No. 9,011,883).

In addition, glutamine is safe, well absorbed, and has no documented side effects. Glutamine is known to enhance wound healing. Glutamine and its dipeptides have been used for parenteral and enteral supplementation components in critically ill patients and in other clinical settings. The first uses of sources of glutamine have been employed either through enteral administration (e.g. in a food supplement) or parenteral administration through the intravenous route. At least one study described administration of glutamine to highly vascular areas, such as the peritoneum, where it is readily absorbed by the vasculature. At these locations, L-glutamine prevented the loss of vascularization due to peritoneal suturing that causes devascularization and adhesion formation. Thus, it was thought that glutamine may prevent fibrosis and adhesion formation by uptake of glutamine in the vasculature and preventing the loss of vascularization.

Some embodiments described herein are methods of treating or reducing adhesion formation or hypoxia-associated tissue damage a subject that is undergoing a surgical procedure. Exemplary and non-limiting surgical procedures contemplated herein include surgeries and procedures that affect the subject's head or neck, pelvic cavity, abdominal cavity, thoracic cavity, or one or more of the subject's limbs. Examples of surgeries that affect the pelvic cavity include, but are not limited to myomectomy, oophorectomy, hysterectomy, removal of endometriosis, tubal ligations, in short, any laparoscopic, laparotomic or open surgeries or procedures (including intravaginal procedures of the uterus, such as dilation and curettage, IVF, etc.) involving any of the reproductive organs, including but not limited to the uterus, ovaries, tubes, prostate, urethra, as well as the urinary bladder, the pelvic colon, and the rectum, or any surgeries involving the major arteries, veins, muscles, and nerves, membranes, ligaments or viscera of the pelvic cavity. Examples of surgeries that affect the abdominal cavity include but are not limited to gall bladder removal, liver resection, lap band surgery, anastomosis of the colon, appendectomy, in short, any surgeries involving the stomach, liver, pancreas, spleen, gallbladder, kidneys, and most of the small and large intestines any surgeries involving the major arteries, veins, muscles, and nerves, membranes, ligaments or viscera of the abdominal cavity. Examples of surgeries that affect the thoracic cavity include, but are not limited to, laparoscopic or laparotomic or open cardiovascular surgeries and procedures, lung surgeries, liver surgeries, gall bladder surgeries, any surgeries involving the major arteries, veins, muscles, and nerves, membranes, ligaments, bones or viscera of the thoracic cavity. Examples of surgeries that affect one or more of the subject's limbs include, but are not limited to laparoscopic or laparotomic or open surgeries involving the arms, legs, elbows, shoulders, spine, including, but not limited to any surgeries involving the major arteries, veins, muscles, and nerves, membranes, ligaments, bones or viscera of the, Examples of surgeries that affect the head and neck include but are not limited to laparoscopic or laparotomic or open surgeries and procedures involving the brain eye surgery or procedures, ear, nose and throat, teeth, gums, and jaw surgery or procedures, cosmetic reconstruction surgeries and procedures of the face, head and neck, cosmetic procedures to the teeth, gums and jaw any surgeries involving the major arteries, veins, muscles, and nerves, membranes, ligaments, bones or viscera of the head and neck.

Based on previous studies involving intravenous administration of L-glutamine and dipeptides comprising L-glutamine, a dose of a particular glutamine source may provide from about 0.01 g to about 1.0 g of L-glutamine per patient kilogram, per day. However, doses may be selected to fall outside these upper and lower amounts. Typical doses employing alanyl-glutamine may be the range of about 0.02 g to about 0.5 g of the dipeptide/kg/day. When administering a glutamine source during a surgical procedure, the typical dose for an average adult human patient may provide from about 0.02 g to about 2.0 g or about 0.3 g to about 1.5 g of L-glutamine or alanyl-glutamine. Because glutamine is an innocuous amino acid, large amounts may be administered without any expected side effects.

In some embodiments, the glutamine source includes glutamine or any pharmaceutically acceptable salt thereof. In some embodiments, the source of glutamine includes L-glutamine or is L-glutamine. It is known that L-glutamine has a relatively low water solubility (i.e., about 40 g/L at room temperature) and low stability during storage. Therefore, the source of glutamine may also include further carrier amino acids or glutamine can be incorporated as part of an oligopeptide, which may increase one or both of the solubility of the L-glutamine and stability. The oligopeptide may include any naturally occurring or non-naturally occurring amino acid. Suitable oligopeptides comprise L-glutamine and are capable of being metabolized to provide L-glutamine. Preferably, such peptides will exhibit increased aqueous solubility and increased stability of L-glutamine. Often, such peptides will also exhibit increased resistance to breakdown during sterilization and storage. The oligopeptide comprising L-glutamine may further include cleavable linker peptide moieties known in the art (see, Bohme and Sickinger, *J. Pept. Sci.* 21, pp. 186-200 (2015). These cleavable linkers may be utilized for attachment to various scaffolds and implants and for the administration methods described herein.

In some embodiments, the source of glutamine is L-glutamine incorporated as part of a dipeptide. Such peptides are dipeptides comprising L-glutamine and one of L-alanine, L-glutamine or L-glycine. An alanyl-glutamine dipeptide (glutamine residue at the C-terminal position) has high solubility in water (568 g/L). A glycyl-glutamine dipeptide (glutamine at the C-terminal position) also shows enhanced solubility in water as compared to glutamine (154 g/L). A glutamyl-glutamine dipeptide may also be employed. Thus, in one embodiment, the source of glutamine comprises L-alanyl-L-glutamine. In some embodiments, the source of glutamine is provided as part of an oligopeptide comprising glutamine, wherein the aqueous solubility and aqueous stability of the source of glutamine is the same as or higher than glutamine alone. In other embodiments, the glutamine source is a glutamine conjugate wherein at least one glutamine residue is bound to a compound via an amino ester bond. Examples of such glutamine sources include, but are not limited to, dichloroacetylglutamine, acetylglutamine, butyrylglutamine, pyruvylglutamine, glutamine linked to any other amino acid by a peptide bond, glutamine linked to a small molecule containing a carboxylic or amino function that can form a peptide bond with the carboxylic or one of the amino functions of glutamine, and glutamine conjugated to any other suitable organic acid via an amino ester bond.

Pharmaceutically acceptable preparations of L-glutamine and L-glutamine containing peptides (including L-alanyl-L-glutamine) are commercially available. In addition, L-glutamine containing peptides for use in the methods described herein may also be synthesized according to known methodology and purified and sterilized for pharmaceutical use.

In some embodiments, the source of glutamine is administered with one or more additional active pharmaceutical ingredients. The additional active pharmaceutical ingredient may be administered in the same way as the source of glutamine or by a different suitable parenteral method or enteral method. In some embodiments, the additional one or more active pharmaceutical ingredients are administered with the source of glutamine by the same route of administration prior to, at the same time, or following the administration of the source of glutamine. In other embodiments, the additional one or more active pharmaceutical ingredients are administered with the source of glutamine by a different route of administration prior to, at the same time, or following the administration of the source of glutamine.

In some embodiments, the formulations including the source of glutamine may be a liquid, paste, or gel comprising a glutamine source dissolved in an aqueous phase. Compositions described herein may be in dry, partially hydrated, or fully hydrated form and include a glutamine source plus a pharmaceutically acceptable carrier and/or diluent component such as sterile distilled water, sterile isotonic solutions, sterile physiological saline solutions, or dry buffer and/or salt mixes or concentrates that, when diluted, form such diluent components. The quantity of the glutamine source in the composition will be selected in order to provide for a fully solubilized amino acid or peptide during administration. Further, the quantity of L-glutamine available from the composition when formulated for administration and/or total amount of formulation administered will be selected by the skilled medical provider in order to provide a suitable dose of L-glutamine to the patient.

In certain embodiments, glutamine source formulations will be thickened in order that the formulation will exhibit increased viscosity over a typical liquid formulation suitable for intravenous injection. Such thickened formulations will be in the form of a paste or gel which may be applied directly to selected tissues or regions during a surgical procedure. Suitable pharmaceutically acceptable thickening agents are known and may be employed. Preferably, such an agent will form a hydrogel when hydrated or will form a hydrogel when subjected to a suitable cross-linking agent and is hydrated. Such gel forming components are selected for their biocompatibility and may be resorbable. Examples of suitable thickeners and gel forming agents known to those skilled in the art that have been employed in pharmaceutical formulations include polymers having a hydrophilic component, such as collagen; polyoxyalkylene polymers such as polyethylene oxides, polyvinyl alcohols, polyvinyl pyrrolidones, and polyhydroxyethyl methacrylates; hyaluronates; and various proteins such as albumin, etc. Hemostatic gels, including those that contain fibrinogen or fibrin, may also be used.

Hydrogel formulations allow for an extended delivery of suitable drugs including for example, L-glutamine or di- or tri-peptides containing at least one glutamine residue. Hydrogels typically form a depot, which further allows for a concentrated application of a drug. The hydrogel comprising a source of glutamine may be generated prior to administration and impregnated with the source of glutamine for further implantation. Alternatively, hydrogels that forms in situ after change environment, including pH and temperature. Various physical and chemical cross-linking polymers for in situ hydrogel formation are known in the art. Exemplary and non-limiting hydrogels may include co-polymers comprising blocks of propylene oxide (PPO), poly(lactide-co-glycolic acid) (PLGA), poly (N-isopropylacrylamide), poly(propylene fumarate), poly(caprolactone) and the like (see, for example, Hoare and Kohane, *Polymer.* 49, pp. 1993-2007 (2008)). Suitable hydrogels may also be generated from naturally occurring proteins and peptides, (see, for example Jonker et al., *Chem Mater.* 24, pp. 759-773 (2011) article) The particular hydrogel formulation can be determined by the application site.

In some embodiments, the source of glutamine is formulated as part of an implantable film containing the source of glutamine. The glutamine source may be applied to or impregnated in the surgical implantable film or other surgical implant. For example, the source of glutamine may be formulated as part of a gel and adhered to the exterior of an implant. Implants composed of a material such as woven resorbable cellulose commercially available as INTERCEED® from Ethicon may be impregnated with a liquid or gel formulation of this invention. Other films contemplated include polyesteramide based films (PEA-III) (see, for example, PCT International Application Publication No. WO/2014053542A1). In some other embodiments, the source of glutamine is formulated for topical, transdermal, or for iontophoretic administration.

In some embodiments, the drug load of the source of glutamine within the dosage form is about 2% to about 90%, including each integer within the specified range. In some embodiments, the drug load is about 10% to about 80%. In some embodiments, the drug load is about 20% to about 60%. In some embodiments, the drug load is about 20% to about 50%. In some embodiments, the drug load is about 20% to about 40%. In some embodiments, the drug load is about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, or about 90%.

In some embodiments, the drug is impregnated into an implantable film. In some embodiments, the drug load in the implantable film is about 2% to about 90%, including each integer within the specified range. In some embodiments, the drug load in the implantable film is about 10% to about 80%. In some embodiments, the drug load in the implantable film is about 20% to about 60%. In some embodiments, the drug load in the implantable film is about 20% to about 50%. In some embodiments, the drug load in the implantable film is about 20% to about 40%. In some embodiments, the drug load in the implantable film is about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, or about 90%. In one embodiment the drug load in the implantable film is about 30%. In another embodiment the drug load in the implantable film is about 50%.

In some embodiments, the dosage form comprising a source of glutamine is stable for months or years. In some embodiments, the pharmaceutical dosage forms of a source of glutamine described herein are stable at 25 C and 60% relative humidity (RH) for about one month, about two months, about three months, about four months, about five months, about six months, about nine months, about ten months, about eleven months, about twelve months, or even longer. In another embodiment, the dosage form may also be stored at refrigerated conditions, such as 2-8 degree C., where it is stable for up to about one month, about two months, about three months, about four months, about five months, about six months, about nine months, about ten months, about eleven months, about twelve months, or even longer, such as for about years, about three years, or any amount of time up to about five years.

EXAMPLES

Primary cultures of normal peritoneal fibroblasts (NPF) were established and pre-hypoxia samples were taken to determine levels of HIF-1α and Type 1 Collagen (COL1A1) under normoxic conditions prior to exposure to episodic hypoxic environments. Cultured cells were exposed to episodes of hypoxia (2% O2; 0.5, 1, 2, or 4, 12, 24 and 48 hours), followed by restoration of normoxia (20% $O_2$) and immediate treatment with Ala-Gln (0, 1, 2, or 10 mM). Levels of HIF-1α and COL1A1 were measured at 12 hours and 24 hours following the initiation of hypoxia. All treatments were completed in triplicate.

HIF-1α and COL1A1 levels were determined by ELISA (HIF-1α ELISA (ThermoFisher Scientific) or COL1A1 ELISA (LifeSpan Biosciences), respectively, per the manufacturer's protocol). Data were analyzed with one-way ANOVA followed by Tukey's tests with Bonferroni correction. Results for HIF-1α are in Tables 1-3.

TABLE 1

HIF-1α (pg/mg protein) 12 hours after hypoxia initiation

| Dose AG (mM) | Hypoxia Time (hours) | | | |
|---|---|---|---|---|
| | 0.5 | 1.0 | 2.0 | 4.0 |
| 0.0 | 7.8 | 6.9 | 5.7 | 5.8 |
| 1.0 | 4.2 | 4.6 | 3.3 | 4.9 |
| 2.0 | 4.7 | 2.4 | 3.2 | 4.4 |
| 10.0 | 5.2 | 3.9 | 4.1 | 5.5 |

TABLE 2

HIF-1α (pg/mg protein) 24 hours after hypoxia initiation

| Dose AG (mM) | Hypoxia Time (hours) | | | |
|---|---|---|---|---|
| | 0.5 | 1.0 | 2.0 | 4.0 |
| 0.0 | 5.2 | 7.7 | 5.1 | 5.6 |
| 1.0 | 3.6 | 4.6 | 3.3 | 4.9 |
| 2.0 | 4.1 | 2.4 | 3.2 | 4.4 |
| 10.0 | 3.6 | 3.9 | 4.1 | 5.5 |

TABLE 3

HIF-1α (pg/mg protein) difference from untreated controls

| Dose AG (mM) | Post Hypoxia Initiation (Hr) | Hypoxia Time (hours) | | | |
|---|---|---|---|---|---|
| | | 0.5 | 1.0 | 2.0 | 4.0 |
| 1.0 | 12 | 3.6 | 2.3 | 2.4 | 0.9 |
| 2.0 | 12 | 3.1 | 4.5 | 2.5 | 1.4 |
| 10.0 | 12 | 2.6 | 3.0 | 1.6 | 0.3 |
| Average all doses | 12 | 3.1 | 3.27 | 2.17 | 0.87 |
| 1.0 | 24 | 1.6 | 3.1 | 1.8 | 0.7 |
| 2.0 | 24 | 1.1 | 5.3 | 1.9 | 1.2 |
| 10.0 | 24 | 1.6 | 3.8 | 1 | 0.1 |
| Average all doses | 24 | 1.43 | 4.07 | 1.57 | 0.67 |

As demonstrated in Table 3, cells treated with AG demonstrated a reduction of HIF-1α at 12 and 24 hours as compared to untreated cells for all durations of hypoxia. Similar results were obtained for COL1A1 (data not shown). While the greatest effects on lowering HIF-1α were seen at 60 minutes, some effect was seen at every time point, with more significant effects at 30 minutes to 120 minutes. All concentrations of AG appear to be effective, although somewhat lower doses (e.g. 1.0 mM and 2.0 mM) appear slightly better than higher (e.g. 10.0 mM) doses.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A method of treating or preventing tissue adhesions in a subject that is undergoing a surgical procedure, the method comprising topically administering to the subject during the surgical procedure a therapeutically effective amount of a glutamine source comprising glutamine, a dipeptide comprising glutamine, or a glutamine amino ester conjugate to a tissue that is subject to adhesion formation, wherein a first dose of the glutamine source is administered within about 30 minutes to about 60 minutes after an initial surgical incision during the surgical procedure, one or more additional doses of the glutamine source is administered at fixed intervals of time after the first dose, and one or more doses is administered just prior to closure of the surgical incision.

2. The method of claim 1, wherein the first dose of the glutamine source is administered within about 30 minutes after the initial surgical incision.

3. The method of claim 1, wherein the first dose of the glutamine source is administered within about 60 minutes after the initial surgical incision.

4. The method of claim 3, wherein the fixed interval of time is about 15 minutes, about 30 minutes, about 45 minutes, about 60 minutes, about 90 minutes, or about 120 minutes after the first dose.

5. The method of claim 4, wherein the fixed interval of time is about 30 minutes after the first dose.

6. The method of claim 1, wherein the surgical procedure affects the abdominal cavity of the subject.

7. The method of claim 1, wherein the surgical procedure affects the thoracic cavity of the subject.

8. The method of claim 1, wherein the surgical procedure affects the head, neck, or spine of the subject.

9. The method of claim 1, wherein the surgical procedure affects one or more limbs of the subject.

10. The method of claim 1, wherein the glutamine source is L-glutamine.

11. A method of treating or preventing hypoxia-associated tissue damage in a subject that is undergoing a surgical procedure, the method comprising topically administering to the subject during the surgical procedure a therapeutically effective amount of a glutamine source comprising glutamine, a dipeptide comprising glutamine, or a glutamine amino ester conjugate to a tissue subject to hypoxia-associated tissue damage, wherein a first dose of the glutamine source is administered within about 30 minutes to about 60 minutes after an initial surgical incision during the surgical procedure, one or more additional doses of the glutamine source is administered at fixed intervals of time after the first dose, and one or more doses is administered just prior to closure of the surgical incision.

12. The method of claim 11, wherein the first dose of the glutamine source is administered within about 30 minutes after the initial surgical incision.

13. The method of claim 11, wherein the first dose of the glutamine source is administered within about 60 minutes after the initial surgical incision.

14. The method of claim 13, wherein the fixed interval of time is about 15 minutes, about 30 minutes, about 45 minutes, about 60 minutes, about 90 minutes, or about 120 minutes after the first dose.

15. The method of claim 14, wherein the fixed interval of time is about 30 minutes after the first dose.

16. The method of claim 11, wherein the surgical procedure affects the abdominal cavity of the subject.

17. The method of claim 11, wherein the surgical procedure affects the thoracic cavity of the subject.

18. The method of claim 11, wherein the surgical procedure affects the head, neck, or spine of the subject.

19. The method of claim 11, wherein the surgical procedure affects one or more limbs of the subject.

20. The method of claim 11, wherein the glutamine source is L-glutamine.

21. A method for reducing HIF-1α in hypoxia-associated damaged tissue in a subject that is undergoing a surgical procedure, the method comprising topically administering to the subject during the surgical procedure a therapeutically effective amount of a glutamine source comprising glutamine, a dipeptide comprising glutamine, or a glutamine amino ester conjugate to the damaged tissue, wherein a first dose of the glutamine source is administered within about 30 minutes to about 60 minutes after an initial surgical incision during the surgical procedure, one or more additional doses of the glutamine source is administered at fixed intervals of time after the first dose, and one or more doses is administered just prior to closure of the surgical incision.

22. The method of claim 21, wherein the first dose of the glutamine source is administered within about 30 minutes after the initial surgical incision.

23. The method of claim 21, wherein the first dose of the glutamine source is administered within about 60 minutes after the initial surgical incision.

24. The method of claim 21, wherein the fixed interval of time is about 15 minutes, about 30 minutes, about 45 minutes, about 60 minutes, about 90 minutes, or about 120 minutes.

25. The method of claim 21, wherein the fixed interval of time is about 30 minutes.

\* \* \* \* \*